United States Patent [19]

Naef

[11] Patent Number: 5,177,085
[45] Date of Patent: Jan. 5, 1993

[54] DIHYDRO-ISOQUINOLINE DERIVATIVES, PROCESSES FOR THEIR PRODUCTION, PHARMACEUTICAL COMPOSITIONS CONTAINING THEM, AND THEIR USE IN TREATING ASTHMA

[75] Inventor: Reto Naef, Rheinfelden, Switzerland

[73] Assignee: Sandoz Ltd., Basel, Switzerland

[21] Appl. No.: 805,662

[22] Filed: Dec. 12, 1991

[30] Foreign Application Priority Data

Dec. 13, 1990 [GB] United Kingdom ............... 9027055

[51] Int. Cl.$^5$ ............... A61N 31/47; C07D 217/16
[52] U.S. Cl. ............................ 514/307; 546/144
[58] Field of Search .................. 546/144; 514/307

[56] References Cited

U.S. PATENT DOCUMENTS 3,891,654  6/1975  Valette ............................ 546/144
4,785,104  11/1988  Rabloczky et al. ............ 546/144
4,980,359  12/1990  Hasspacher et al. ........... 546/144

FOREIGN PATENT DOCUMENTS 251361  1/1988  European Pat. Off. .

*Primary Examiner*—C. Warren Ivy
*Assistant Examiner*—James H. Turnipseed
*Attorney, Agent, or Firm*—Gerald D. Sharkin; Robert S. Honor; Joseph J. Borovian

[57] ABSTRACT

6,7-Di($C_{1-4}$alkoxy)-1-[3,5-di($C_{1-4}$alkoxy)phenyl]-3,4-dihydro-3-hydroxy-methyl-isoquinolines, their physiologically hydrolyzable and -acceptable esters and acid addition salts thereof are novel. The said compounds and esters and pharmaceutically acceptable acid addition salts thereof are useful as pharmaceuticals, e.g. in the treatment of asthma.

10 Claims, No Drawings

DIHYDRO-ISOQUINOLINE DERIVATIVES, PROCESSES FOR THEIR PRODUCTION, PHARMACEUTICAL COMPOSITIONS CONTAINING THEM, AND THEIR USE IN TREATING ASTHMA

The present invention relates to novel dihydro-isoquinoline derivatives having pharmaceutical utility, processes for their production, pharmaceutical compositions comprising them and their use as pharmaceuticals.

More particularly the present invention provides a compound of formula I

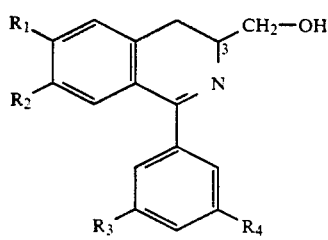

wherein $R_1$ to $R_4$ are each independently $C_{1-4}$alkoxy, or a physiologically hydrolyzable and -accepable ester thereof, or an acid addition salt of such a compound or ester.

In the compounds of formula I, alkoxy groups and moieties may be branched or straight chain. Suitably they are straight chain. Most preferably $R_1$ to $R_4$ are each methoxy.

By "physiologically hydrolyzable and -acceptable ester" as used herein is meant an ester in which the hydroxy group at the 3-position is esterified and which is hydrolyzable under physiological conditions to yield an acid which is itself physiologically tolerable at dosages to be administered. The term is thus to be understood as defining regular pro-drug forms. Examples of such esters include for example the 3-acetates, as well as -benzoates of the formula I compounds.

Compounds of formula I and their esters as aforesaid exist in both free and acid addition salt form. Suitable pharmaceutically acceptable acid addition salt forms for use in accordance with the present invention include, for example, the hydrochloride, oxalate and fumarate salts.

The 3-position carbon atom of compounds of formula I is asymmetric. The compounds of the invention thus exist in enantiomeric form, i.e. as optically active antipodes having the [3S] or [3R] configuration. In relation to formula I these may be represented as follows:

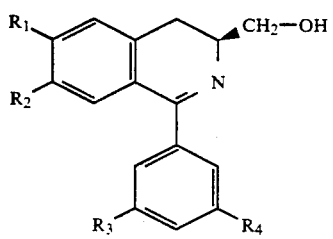

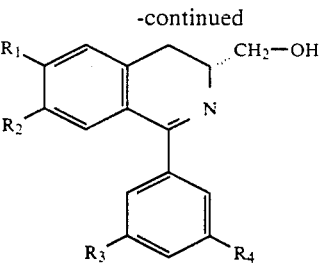

Formula IA represents the [3S]-enantiomer and formula IB the [3R]-enantiomer. Unless otherwise specified, the present invention is to be understood as embracing both individual [3S] and [3R] enantiomers as well as mixtures, e.g. racemic mixtures, of the compounds of formula I, their esters and acid addition salts as aforesaid.

In general, for pharmaceutical use in accordance with the present invention, the [3S] enantiomer of the compounds of the invention will be preferred. Thus the preferred compound of formula I is [3S] 3,4-dihydro-6,7-dimethoxy-1-(3,5-dimethoxy-phenyl)-3-hydroxymethyl-isoquinoline [Formula IA: $R_1$ to $R_4$ all $=CH_3O-$].

Accordingly, in a preferred embodiment, the present invention provides a compound of formula I as hereinbefore defined in [3S] enantiomeric form, for example, in pure or substantially pure [3S] enantiomeric form (e.g. comprising 80% or more, preferably 90% or more, especially 95 or 98% or more of the pure [3S] enantiomer), or physiologically hydrolyzable or -acceptable ester thereof or acid addition salt of such a compound or ester.

Individual enantiomers of compounds of the invention may be obtained in conventional manner, e.g. employing optically active starting materials, or by separation of initially obtained racemates for example as hereinafter described.

In a further aspect the present invention also provides a method for the production of compounds of the invention which method comprises:

a) for the production of a compound of formula I as defined above, removing the protecting group from a compound of formula I as defined above in 3-hydroxy protected form, i.e. from a compound of formula II

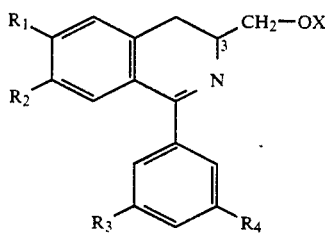

wherein $R_1$ to $R_4$ have the meanings given for formula I and X is a hydroxy protecting group; or b) for the production of a physiologically hydrolyzable and -acceptable ester of a compound of formula I as defined above, esterifying a compound of formula I as defined above; and recovering the obtained compound of formula I or ester thereof in free or acid addition salt form.

Process step (a) may be performed in accordance with methods known and practiced in the art for the removal of hydroxy-protecting groups. Suitable hydroxy protecting groups as X include any of those known and commonly employed in the art, for example benzoyl or substituted benzoyl groups, in particular 3,5-dialkoxy benzoyl groups in which the alkoxy moieties correspond to $R_3$ and $R_4$ of formula I.

Such groups are for example suitably removed by hydrolytic cleavage, e.g. in the presence of aqueous lithium hydroxide and a lower alkanol, e.g. at temperatures of from 0° to 50° C.

Esterification in accordance with process step (b) may also be conducted in accordance with standard procedures, e.g. by reaction of a compound of formula I with an appropriate acid halide or anhydride in the presence of a base, for example an amine or alkali metal carbonate. The reaction is suitably carried out in an inert solvent or diluent, e.g. at a temperature of from 0° to 120° C., under an inert atmosphere.

Where the product obtained by the above processes comprises a mixture of enantiomers, e.g. racemic mixture, the individual enantiomers may, if desired, be separated by conventional procedures, e.g. resolution by crystallization using optically active acids or chromatographic separation using a chiral stationary phase, to yield the [3S] or [3R] enantiomer in pure or substantially pure form. Alternatively the pure enantiomers may be prepared directly from the corresponding optically pure starting material, e.g. a compound of formula II in [3S] enantiomeric form, for example as described in the accompanying example.

The hydroxy protected derivatives of formula II employed as starting materials for process step (a) are also new and form part of the invention. They may be prepared in accordance with the following reaction sequence:

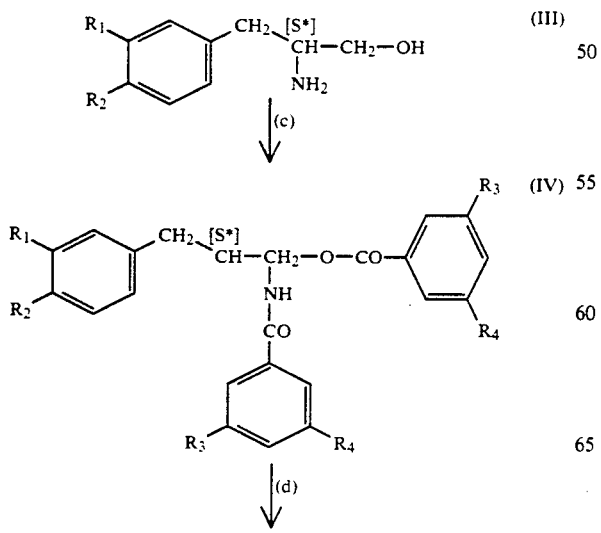

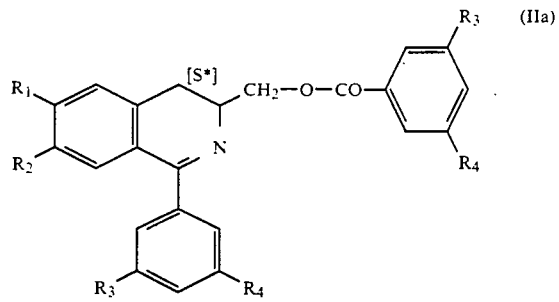

In the above formula IIa, the hydroxy protecting group X of formula II is 3,5-di($C_{1-4}$alkoxy)-benzoyl as shown. This enables the introduction of both the protecting group and the amide group (which are identical) at step (c). It will however be appreciated that the above scheme may be adapted to permit introduction of any other hydroxy protecting group at step (c).

Step (c) as represented above involves reaction of (III) with a compound of formula V

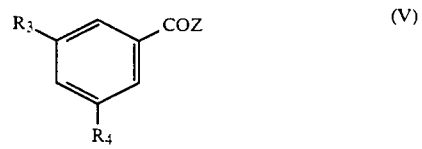

wherein $R_3$ and $R_4$ have the meanings given for formula I and Z is a leaving group to effect concomitant esterification and amidation.

Suitable compounds of formula V include both halides (Z=halogen, for example chlorine) and anhydrides (Z=3-($R_3$)-5-($R_4$)-benzoyloxy). Reaction is appropriately performed at a temperature of from −20° to 50° C., in an inert solvent or diluent such as dichloromethane, and in the presence of a base, for example a dialkylaminopyridine.

Process step (d) comprises dehydrative cyclization of IV. This may also be achieved by methods known in the art, for example, by reaction of IV with a phosphoroxy trihalide in the presence of an inert solvent or diluent such as acetonitrile at temperatures of from e.g. 50° C. to reflux.

By application of the above procedures starting with the racemic compound III, formula I compounds, esters and salts in racemic form may be obtained. Alternatively, starting with the pure [S] or [R] enantiomer of III, the pure or substantially pure [3S] or [3R] formula I compounds, esters and salts may be obtained.

The required starting materials of formulae III (both in racemic and individual [S] and [R] enantiomeric form) are known from the art [cf. Schrecker et al., J. Amer. Chem. Soc. 79, 3827–3828 (1957) and Seki et al., Chem. Pharm. Bull. (Tokyo) 15 (12), 1948–1954 (1967)] or may be prepared analogously to the known compounds.

The following examples are illustrative of the procedures of the present invention:

EXAMPLE 1

Preparation of [3S] 3,4-dihydro-6,7-dimethoxy-1-(3,5-dimethoxyphenyl)-3-hydroxymethyl-isoquinoline.

Step (a)

A suspension of 98.4 g of [3S] 3,4-dihydro-6,7-dimethoxy-3-[(3,5-dimethoxybenzoyloxy)methyl]-1-(3,5-dimethoxyphenyl)-isoquinoline [Formula IIa: all of $R_1$ to $R_4$=methoxy], 51 $CH_3OH$ and 207 ml aqueous lithium hydroxide, is stirred for 12 hrs. at room temperature. The obtained solution is concentrated under reduced pressure, treated with ethyl acetate and washed with $H_2O/Na_2CO_3$. The organic phase is dried over $K_2CO_3$ and the solvent removed under reduced pressure. The residue is taken up in ethyl ether, crystallized, filtered and dried to yield the title compound: m.p.=59°–62° C., $\alpha_D^{20}$= −55.19° (c=0.5 in $CH_3OH$).

The obtained free base may be salified and the obtained salt re-crystallized in conventional manner. Thus the title compound is also prepared in the following salt forms:

a) Hydrogen maleinate salt: m.p.=141°–142° C., $\alpha_D^{20}$= +154° (c=0.5 in $CH_3OH$);
b) Hydrochloride salt: m.p.=202°–204° C., $\alpha_D^{20}$= +166° (c=0.5 in $CH_3OH$);
c) Hydrogensulfate salt: m.p.=181°–184° C., $\alpha_D^{20}$= +152° (c= 0.5 in $CH_3Oh$).

The starting material for the above process is prepared as follows:

Step (c)

204g of 3,5-dimethoxybenzoyl chloride in 700ml $CH_2Cl_2$ are added to 86g [2S]2-amino-3,4-dimethoxyphenyl)-propanol [formula III: $R_1$ and $R_2$ both =methoxy] 4.9g 4-dimethyl aminopyridine in 159g triethylamine and 2.3 1 $CH_2Cl_2$ at 3° C. The reaction mixture is raised to room temperature over 12 hrs., washed with 5% aqueous tartaric acid and 10% $H_2O/NaHCO_3$, and the organic phase dried over $Na_2SO_4$. The solvent is removed under reduced pressure and the residue crystallized feom ehtyl ether to yield the product, [2S]2-(3,5-dimethoxybenzoylamino)-3-(3,4-dimetyoxy phenyl)-propyl 3,5-dimethoxy-benzoate [Formula IV: all of $R_1$ to $R_4$=methoxy]: m.p. =171°–174° C.

Step (d)

159g of the product of step (c) in 134g phospyoroxy trichloride and 925ml acetonitrile are heated to reflux for 3 hrs. The solvent is removed under reduced pressure the residue treated with 10% $NaHCO_3$ and extracted with ethyl acetate. The organic phase is dried over $Na_2SO_4$ and solvent removed under reduced pressure. The residue is purified chromatographically on silica gel using hexane/ethyl acetate (1:1) as mobile phase to yield the starting material to step (a): m.p. =101°–108° C.

Racemic 3,4-dihydro-6,7-dimethoxy-1-(3,5-dimethoxyphenyl)-3-hydroxymethyl-isoquinoline is prepared analohously to steps (c) to (a) above starting from racemic 2-amino-3-(3,4--dimethoxy-phenyl)-propanol at step (c): m.p. for the hydrochloride =214°–217° C.

EXAMPLE 2

Preparation of [3S]3,4-dihydro-1-(3,5-diisopropyloxy-phenyl)-3-hydroxymethyl-6-isopropyloxy-7-isoquinoline The title compound is prepared analogously to the procedures described in example 1, but employing 3,5-diisopropylozybenzoyl chloride and [2S]2-amino-3-(3-isopropyloxy-4-methoxyphenyl)-propanol as starting materials at Step (c). $[\alpha]^{20}_D$ for the free base = +155°(c=0.5 in methanol).

Compounds of formula I, their physiologically hydrolyzable and-acceptable esters and the pharmaceutically acceptable acid addition salts of said compounds and esters (referred to below for conventience collectively as "COMPOUNDS I, ESTERS AND/OR P.A. SALTS") exhibit pharmacological activity and are therefore indicated for use as pharmaceutical agents, e.g., for therapy. In particular they exhibit bronchodilator and asthma-prophylactic as well as anti-inflammatory properties. These properties may be demonstrated in standard tests in vivo and in vitro, for example as follows:

EXAMPLE A: BRONCHODILATOR ACTIVITY

1. Bronchospasmolytic Activity in vitro

1. Relaxation of Guinea-Pig Tracheal Smooth Muscle

Guinea-pigs (Dunkin-Hartley, 350–500gm) are killed with Pentothal (100mg/kg i.p.). The trachea is dissected and a section 2–3cm in length excised. The trachea is transected in the transverse plane at alternate cartilage plates so as to give rings of tissue 3–5mm in depth. The proximal and distal rings are discarded. Individual rings are mounted vertically on stainless steel supports, one of which is fixed at the base of an organ bathm the other being attached to an isometric transducer. The rings are bathed in Krebs solution composition mM: $NaHCo_3$25, NaCl 113, KCl 4.7, $MgSO4.7H_2O$ 1.2, $KH_2PO_4$1.2, $CaCl_2$2.5, Glucose 11.7) at 37° C. and gassed with $O_2/CO_2$ (95:5,v/v). Rings prepared in this manner, preloaded with 1 g, generate spontaneous tone and, after a period of equilibration (45–60 min.), relax consistently on addition of spasmolytic drugs. To ascertain spasmolytic activity, test substances are dissolved in physiological saline and added in increasign quantities to the organ bath at 5 min. intervals to provide a cumulative concentration-effect curve.

In the above test model COMPOUNDS I, ESTERS AND P.A. SALTS produce concentration-related relaxation of guinea-pig tracheal ring preparations at concentrations of from about 0.001 to 1.0 $\mu$ m. No further relaxation is produced by isoprenaline and relaxation is fully reversed by washing.

1.b Relaxation of human bronchus

The test is performed analogously to 1. a above but employing rings of human bronchus dissected from lung that has been resected for carcinoma. Dissected material is used immediately or first immersed in total calf serum containing DMSO (1.8$\mu$), slowly frozen to −70° C. and stored in liquid $N_2$ at −190° C. For use, stored rings are thawed for 30 mins. at room temperature and 3 mins. at 37° C.

In the above test model COMPOUNDS I, ESTERS AND P.A. SALTS produce concentration-related relaxation of human bronchus ring preparations at concentrations of from 0.1 to 10.0 $\mu$ M.

2. Bronchodilator Activity in vivo

Guinea pigs (Dunkin-Hartley, male, 400–600g) are anesthetized with phenobarbital (100-mg/kg i.p.) and pentobarbital (30 mg/kg i.p.) and paralyzed with gallamine (10 mg/kg i.m.). Animals are ventilated via a tracheal cannula (10 ml/kg, 1 Hz) with a mixture of air and oxygen (1:1 v/v). Blood pressure and heart rate are recorded at the carotid artery. Ventilation is monitored by a Fleisch flow transducer in line with the inspiratory circuit. When making measurements of flow, coincident pressure changes in the thorax are monitored directly via an intrathoracic trochar, permitting display of differential pressure relative to the trachea. From this information in relation to flow and differential pressure, resistance [$R_l$] and compliance [$D_{dyn}$] are calculated using a digital respiratory analyzer for each respiratory cycle.

Bombesin [300–600mg/kg] is administered as a bolus injection intravenously, thereby causing bronchospasm which is sustained over several minutes. When bronchospasm has achieved a plateau [at 1–2 mins.], test substance is introduced into the jugular vein via an indwelling cannula. The bronchodilator response is taken as the percentage reduction (measured at both 1 and 3 mins.) of the maximal response to bombesin.

In the above test model COMPOUNDS I, ESTERS AND P.A. SALTS cause significant bronchodilator response at dosages of from about 0.01 to about 0.1 mg/kg i.v..

EXAMPLE B: SUPPRESSION OF AIRWAYS HYPERREACTIVITY

PAF-Treated Animals

Guinea-pigs are anesthetized and prepared for recording of lung function as described under Example A.2. above. Intravenous injection of low dose histamine (1.0–1.8 µg/kg) established airways sensitivity to spasmogens. Following infusion of PAF (platelet activating factor) over 1 hr. (total dose=600 ng/kg), injection of low dose bombsin 20 mins. after cessation of infusion reveals development of airways hyperreavtivity, which is expressed as the paired difference between the maximal response amplitude before and after PAF exposure.

On administration of COMPOUNDS I, ESTERS AND P.A. SALTS by infusion during PAF exposure at dosages of from about 0.01 to about 0.1 mg/kg, suppression of PAF-induced airways hyperreactivity is observed.

EXAMPLE C: INHIBITION OF HUMAN PHOSPHODIESTERASE (PDE) ISOENZYMES

Phosphodiesterase isoenzymes have been classified according to their tissue distribution, substrate specificity and affinity as well as their susceptibility to selective inhibition by known inhibitor compounds. On this basis, five classes of PDE isoenzymes have been defined: PDE isoenzymes types I through V [Beavo et al., TIPS 11, 150–155 (1991) and Nicholson et al., TIPS 12, 19–27 (1990)]. Tpye III PDE inhibitors are known to be relaxants of human airways smooth muscle. Type IV PDE inhibitors are reported to have potent anti-inflammatory actions [Murray et al. Agents and Actions Supplements 34, 27–46 (1991)]. Moreover, elevation of PDE isoenzymes corresponding to types III and IV has been reported as a characteristic feature of leucocytes taken from atopic subjects [Hanafin et al., Drug. Develope. Res., 13, 123–126 (1988)]. Compounds having high selectivity for PDE isoenzymes of Types III and IV may be anticipated to exhibit bronchodilator and asthma prophylactic as well as anti-inflammatory properties.

Citrated human blood was collected and neutrophils obtained by dextran sedimentation, density gradient centrifugation on a mixture of Histopaque 1077 and 1119 with a final density of 1.089 g/l and hypotonic lysis of erythrocytes. Human platelets from the same source are washed with PBS (NaCl 140 mM, KCl 2.7 mM, $KH_2PO_4$ 1.5 mM, $Na_2HPO_4$ 8.1 mM, pH 7.4). Neutrophils and platelets are suspended in 10 ml of buffer (0.24 M sucrose, 1 mM EDTA, 1 mM dithiothreitol, 10 mM tris HCl, pH 7.4) containing the following protease inhibitor solutions: 5 µl/ml of phenylmethylsulphonylfluoride (7 mg/ml in 2-propanol), 1 Nl/ml leupeptin and pepstatin A (1 mg/ml each, in ethanol). After sonication (15 sec ar 4° C.) using a probe sonicator, homogenates are centrifuged (2200 g). The pellet is resuspended in 10 ml of buffer and the sonication repeated. Pooled supernatants are stored at −20° C. Phosphodiesterase activity is assayed by the ion-exchange column method [Thompson et al., Nucleotide Research 10, 69–92 (1979)], using 1µM [$^3$H]-cyclic AMP as substrate.

According to the classification of Beavo et al., loc. cit., PDE activity in neutrophils is categorized as type IV (low $K_m$ cyclic AMP PDE), whereas platelets contain predominantly type III PDE (cyclic GMP-sensitive) and enzyme preparations from human lung comprise type V PDE.

In these preparations, COMPOUNDS I, ESTERS AND P.A. SALTS show greater selectivity for type III, type IV and type V PDE isoenzymes as compared, for example, with the known anti-asthma drug aminophylline.

EXAMPLE D: ANTIINFLAMMATORY ACTIONS-INHIBITION OF SECRETION OF $H_2O_2$ BY ADHERENT HUMAN NEUTROPHILS

Leukocyte-enriched blood cell preparations (buffy coat from 400 ml of blood) are obtained from a blood bank. After hypotonic lysis of erythrocytes, leukocytes are suspended in 20 ml phosphate buffered saline (PBS), distributed into four 15 ml polypropylene tubes and underlaid with a discontinuous density gradient consisting of 5 ml of Histopaque 1089 (from a mixture of 12 ml of Histopaque 1119 and 30 ml of Histopaque 1077). Centrifugation (10 min. at 2000 g, room temperature) yields a band on the interface consisting of mononuclear blood cells and a pellet of >90% neutrophils as verified by differential cell count of May-Grünwald stained smears. Neutrophils are suspended in Krebs-Ringer at $6 \times 10^5$ ml. 96 well microtitre plates are coated with 50 µl/well of a 1 µg/ml solution of fibronection in PBS and incubated for 4h at 37° C.

Before use, wells are rinsed once with 100 µl Krebs-Ringer. Each well is loaded with inhibitor in 0.6% dimethylsufoxide (DMSO) (final concentration of DMSO 0.15%, showing no effect when compared to wells without DMSO), 42 pmol N-formyl-Met-Leu-Phe fMLP, 5 µg horseradish peroxidase, 50 µg sodium azide, 5 µg of scopoletin and 15,000 neutrophils in a final volume of 0.1 ml. Plates are held at 37° C. during 2 hours, after which fluorescence (excitation 365 nm, emission 460 nm) is read.

To calculate the effect of inhibitors, DMSO-treated controls are used to represent 0% inhibition, and wells without cells are used to represent 100% inhibition (i.e. no fluorescence loss).

The chemotactic peptide fMLP induces secretion of large amounts of hydrogen peroxidase from adherent human neutrophils, or reaction than can be detected by scopoletin oxidation indicating cell activation.

In this test method, COMPOUNDS I, ESTERS AND P.A. SALTS strongly inhibit H$_2$O$_2$ secretion at concentrations of the order of 1.0 to 10.0 μM.

In addition to the foregoing, general pharmacological testing indicates that COMPOUNDS I, ESTERS AND P.A. SALTS exhibit a marked and surprisingly improved profile in relation to intended therapeutic uses compared with other known compounds, e.g. of related structure, for example, reduced influence on behavioral response, e.g. in male OFA mice and/or reduced cardiovascular side effect, for example in relation to hemodynamic parameters. COMPOUNDS I, ESTERS AND P.A. SALTS also show advantage as exhibited, e.g. in toxicity acute tolerability studies in the dog and in primates.

Having regard to their bronchodilator activity as well as their profile in relation to PDE isoenzyme inhibition, COMPOUNDS I, ESTERS AND P.A. SALTS are useful as bronchodilators, e.g. for the treatment of broncho-constriction (chronic or acute). As bronchodilators they are, in particular, useful for the symptomatic treatment, of obstructive or inflammatory airways disease.

Having regard to their activity in inhibiting airways hyperreactivity or in diminishing basal or on-going airways hyperreactivity, their anti-inflammatory properties and their profile in relation to PDE isoenzyme inhibition, COMPOUNDS I, ESTERS AND P.A. SALTS are useful in the prophylactic treatment of obstructive or inflammatory airways disease. Thus COMPOUNDS I, ESTERS AND P.A. SALTS may be used prophylactically, suitably by continued and regular administration over longer periods of time, to provide advance protection against recurrence of broncho-constrictor attack consequential to obstructive or inflammatory airways disease including specific such diseases as hereinafter specified or for the control, restriction or reversal of basal status of such disease.

The words "treatment" and "treating" as used throughout the present specification and claims in relation to obstructive or inflammatory airways disease are to be understood accordingly as including both symptomatic and prophylactic modes of treatment or therapy as discussed above.

In accordance with the foregoing the present invention also provides:

IA. A method of effecting bronchodilatation in a subject in need thereof which method comprises administering to said subject an effective amount of a COMPOUND I, ESTER OR P.A. SALT; as well as IB. A method of treating, e.g. inhibiting or ameliorating, airways hyperreactivity in a subject in need thereof, which method comprises administering to said subject effective amount of a COMPOUND I, ESTER OR P.A. SALT.

In the alternative the present invention provides:

II. A COMPOUND I, ESTER OR P.A. SALT for use as a pharmaceutical, for example for use as a bronchodilator or for use in treating, e.g. inhibiting or ameliorating airways hyperreactivity.

The present invention in particular provides a method, e.g. as defined under IA and/or IB above, for the treatment of obstructive or inflammatory airways disease including, asthma, pneumoconiosis and chronic obstructive airways disease (COAD) as well as exacerbation of airways hyperreactivity consequent to other drug therapy.

The present invention especially provides a method for the treatment of asthma of whatever type or genesis. It is applicable to both intrinsic and, especially, extrinsic asthma. It is especially applicable to the treatment of allergic (atopic, i.e. IgE-mediated), asthma. It is also applicable to the treatment of non-atopic, as well as bronchitic asthma, excercise induced asthma, occupational asthma, asthma induced following bacterial infection and other non-allergic asthmas. Treatment of asthma is also to be understood as embracing treatment of subjects, e.g. of less than 4 or 5 years of age, exhibiting wheezing symptoms, in particular at night, and diagnosed or diagnosable as "wheezy infants", an established patient category of major medical concern and now more correctly identified as incipient or early-phase asthmatics. (For convenience this particular asthmatic condition is referred to as "wheezy-infant syndrome").

The present invention also provides a method for the treatment of pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and, in particular, byssinosis.

The present invention further provides a method for the treatment of COAD or exacerbation of airways hyperreactivity consequent to other drug therapy, in particular other inhaled drug therapy, for example, β-agonist bronchodilator drug therapy.

The present invention also provides a method, e.g. as defined under IA above for the treatment of chronic or acute bronchoconstriction or airways obstruction, as well as of diseases or conditions characterized by such bronchoconstriction, for example chronic obstructive pulmonary disease (COPD) including chronic bronchitis and pulmonary emphysema or dyspnea associated therewith. The present invention is also applicable to the treatment of bronchitis of whatever type or genesis, including, for example, acute bronchitis, arachidic bronchitis, catarrhal bronchitis, chronic bronchitis, croupous bronchitis, phthinoid bronchitis and so forth.

The present invention thus further provides:

II A method for the treatment (including symptomatic and/or prophylactic treatment as the case may be) of any disease or condition as hereinbefore set forth, which method comprises administering to a subject in need thereof an effective amount of a COMPOUND I, ESTER OR P.A. SALT; as well as III A COMPOUND I, ESTER OR P.A. SALT for use in any disease or condition as hereinbefore set forth.

Having regard to their profile in relation to inhibition of PDE isoenzymes, in particular their profile as type IV PDE inhibitors, COMPOUNDS I, ESTERS AND P.A. SALTS are also indicated for use as type IV PDE inhibitors, for example: for the treatment of inflammatory and allergic diseases such as rhinitis, conjunctivitis, atopic dermatitis, urticaria and gastro-intestinal allergies; as vasodilators, e.g. for the treatment of angina, hypertension, congestive heart failure and multi-infarct dementia; and for the treatment of other conditions where PDE IV inhibition is indicated, for example, depression, conditions and diseases characterized by impaired cognitive function including Alzheimer's disease, Parkinson's disease, rheumatic and other inflammatory disease, stroke, heterograft rejection and other immune related diseases, in particular autoimmune diseases such as autoimmune hematological disorders (including e.g. hemolytic anemia, aplastic anemia, pure red cell anemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine ophthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy). COMPOUNDS I, ESTERS AND P.A. SALTS are further indicated for use in the treatment or therapy of adult respiratory distress syndrome (ARDS) and bronchiolitis.

COMPOUNDS I, ESTERS AND P.A. SALTS are also indicated for use as anti-tumor agents as may, for example, be indicated by their activity in human cell line cytotoxicity tests against human tumor cell lines as well as clonogenic assay.

Dosages employed in practicing the various methods of the present invention will of course vary depending, e.g., on the particular condition to be treated, the particular COMPOUND I, ESTER AND P.A. SALT employed, the mode of administration and the therapy desired. In general however satisfactory results, e.g. for bronchodilator effect and/or effect in relation to airways hyperreactivity, are indicated to be obtained at dosages of from about 0.15 to about 2.8 mg/kg/p.o. In larger mammals, for example humans, an indicated daily dosage for oral administration, in particular as bronchodilator agents or as agents for the inhibition or amelioration of airways hyperreactivity, e.g. for such use in diseases or conditions as hereinbefore described, in particular for use in obstructive or inflammatory airways disease, especially asthma, will be in the range of from about 10 to about 200 mg, in particular from about 50 to 100 mg conveniently administered once or in divided doses 2 to 4×/day or in sustained release form. Unit dosage forms for oral administration thus suitably comprise from about 2.5 to about 200, in particular from about 12.5 to about 50 or 100 mg of COMPOUND I, ESTER OR P.A. SALT, together with a pharmaceutically acceptable diluent or carrier therefor.

COMPOUNDS I and ESTERS may be administered in free base form or in pharmaceutically acceptable acid addition salt form. Such salts (i.e. P.A. SALTS) exhibit the same order of activity as the free bases.

COMPOUNDS I, ESTERS OR P.A. SALTS may be administered by any conventional route, suitable or appropriate to the condition or disease to be treated, e.g. nasally, enterally, topically, orally, e.g. in the form of tablets or capsules, or parenterally, e.g. in the form of injectable solutions or suspensions. They may also, in particular, be administered by the pulmonary route, especially where diseases or conditions of the airways are to be treated, for example for bronchodilator effect or for the inhibition or amelioration of airways hyperreactivity.

In accordance with the foregoing the present invention also provides: a pharmaceutical composition comprising a COMPOUND I, ESTER OR P.A. SALT together with a pharmaceutically acceptable diluent or carrier therefor, e.g. for use in any method as defined above. Such compositions may be manufactured in conventional manner.

As previously indicated, the therapeutic dosage requirement for COMPOUNDS I, ESTERS AND P.A. SALTS will depend on a variety of factors. Dosaging for any particular COMPOUND I, ESTER OR P.A. SALT will also depend upon its relative potency of action. For the preferred compound of the invention, namely the product of EXAMPLE 1 in pure or substantially pur [3S] enantiomeric form, results in individual experiments performed in accordance with EXAMPLES A and B above in comparison with the known anti-asthmatic drug substance aminophylline were as follows:

EXAMPLE A.1.a $IC_{50}$ (concentration required to increase relaxation by 50%)=

For product of EXAMPLE 1: 0.18 $\mu$M
For aminophylline: 130.0 $\mu$M

EXAMPLE A.1.b $IC_{50}=$
For product of EXAMPLE 1: 1.9 $\mu$M
For aminophylline: 158 $\mu$M

EXAMPLE B $ID_{50}$ (dose required to increase relaxation by 50%)=
For product of EXAMPLE 1: ca. 0.05 mg/kg/i.v.
For theophyline: 3.0 mg/kg/i.v.

For bronchodilator usage indicated daily dosages of the EXAMPLE 1 compound in pure or substantially pure [3S] enantiomeric form will thus be of the order of from about 1/100th to about 1/500th of those conventionally used employing aminophylline.

I claim:

1. A compound of formula I

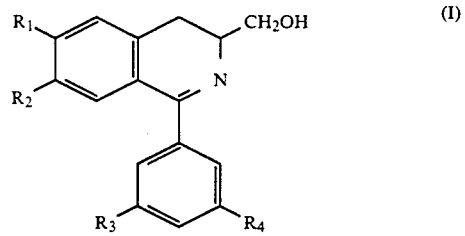

wherein $R_1$ to $R_4$ are each independently $C_{1-4}$ alkoxy, or a physiologically hydrolyzable and -acceptable ester thereof, or an acid addition salt of such a compound or ester.

2. A compound as claimed in claim 1 wherein, in formula I, $R_1$ to $R_4$ are each methoxy, or a physiologically-hydrolyzable and -acceptable ester thereof or an acid addition salt of such a compound or ester.

3. A compound as claimed in claim 1 in [3S] enantiomeric form, or a physiologically-hydrolyzable and -acceptable ester thereof or an acid addition salt of such a compound or ester.

4. A compound as claimed in claim 1 which is [3S] 3,4-dihydro-6,7-dimethoxy-1-(3,5-dimethoxy-phenyl)-3- hydroxymethyl-isoquinoline, or an acid addition salt thereof.

5. A compound as claimed in claim 1 which is [3S] 3,4-dihydro-1-(3,5-diisopropyloxy-phenyl)-3-hydroxymethyl-6-isopropyloxy-7-methoxy-isoquinoline, or an acid addition salt thereof.

6. A pharmaceutical composition comprising a compound or ester as claimed in claim 1 or a pharmaceutically acceptable acid addition salt of such a compound or ester, together with a pharmaceutically acceptable diluent or carrier therefor.

7. A method of effecting bronchodilatation in a subject in need thereof which method comprises administering to said subject an effective amount of a compound or ester as claimed in claim 1 or a pharmaceutically acceptable acid addition salt of such a compound or ester.

8. A method for the treatment of airways hyperreactivity in a subject in need thereof which method comprises administering to said subject an effective amount of a compound or ester as claimed in claim 1 or a pharmaceutically acceptable acid addition salt of such a compound or ester.

9. A method for the treatment of obstructive or inflammatory airways disease in a subject in need thereof which method comprises administering to said subject an effective amount of a compound or ester as claimed in claim 1 or a pharmaceutically acceptable acid addition salt of such a compound or ester.

10. A method for the treatment of asthma in a subject in need thereof which method comprises administering to said subject an effective amount of a compound or ester as claimed in claim 1 or a pharmaceutically acceptable acid addition salt of such a compound or ester.

* * * * *